(12) United States Patent
Kumpch et al.

(10) Patent No.: US 10,718,710 B2
(45) Date of Patent: Jul. 21, 2020

(54) WATER ANALYSIS DEVICE

(71) Applicant: HACH LANGE GMBH, Berlin (DE)

(72) Inventors: Hans-Joachim Kumpch, Berlin (DE); Hartmut Draeger, Berlin (DE); Detlef Liebchen, Berlin (DE)

(73) Assignee: HACH LANGE GMBH, Berlin (DE)

( * ) Notice: Subject to any disclaimer, the term of this patent is extended or adjusted under 35 U.S.C. 154(b) by 0 days.

(21) Appl. No.: 16/333,955

(22) PCT Filed: Aug. 28, 2017

(86) PCT No.: PCT/EP2017/071568
§ 371 (c)(1),
(2) Date: Mar. 15, 2019

(87) PCT Pub. No.: WO2018/050428
PCT Pub. Date: Mar. 22, 2018

(65) Prior Publication Data
US 2019/0204219 A1    Jul. 4, 2019

(30) Foreign Application Priority Data

Sep. 15, 2016   (DE) .................... 20 2016 105 143 U

(51) Int. Cl.
| | |
|---|---|
| *G01N 21/51* | (2006.01) |
| *G01N 21/15* | (2006.01) |
| *G01N 33/18* | (2006.01) |

(52) U.S. Cl.
CPC .............. *G01N 21/51* (2013.01); *G01N 21/15* (2013.01); *G01N 33/18* (2013.01); *G01N 2021/158* (2013.01); *G01N 2021/513* (2013.01)

(58) Field of Classification Search
CPC ....... G01N 2021/158; G01N 2021/513; G01N 21/15; G01N 21/51; G01N 33/18
(Continued)

(56) References Cited

U.S. PATENT DOCUMENTS

| | | |
|---|---|---|
| 4,540,102 A | 9/1985 | Wiedmer |
| 5,446,544 A | 8/1995 | Beers |

FOREIGN PATENT DOCUMENTS

| | | |
|---|---|---|
| EP | 0109631 A2 | 5/1984 |
| JP | 2006377106 A | 12/2006 |
| WO | WO2016079259 A1 | 5/2016 |

OTHER PUBLICATIONS

European Patent Office, International Search Report, dated Nov. 8, 2017, 14 pages.

*Primary Examiner* — Tri T Ton
(74) *Attorney, Agent, or Firm* — Ference & Associates LLC

(57) ABSTRACT

A water analysis device having a light source and a light detector for detecting an optical parameter of a water sample in a transparent measuring cell is disclosed. A ventilation circuit for ventilating a cell chamber is provided, wherein there is a differential pressure of at least 2.0 mbar between the cell chamber and the atmosphere when a ventilation pump is operated. The device housing forms the cell chamber which is fluidically sealed by a cover assembly. The cover assembly and the device housing have a mechanism that mimics the sealing action of a turn-lock fastener, such that the cover assembly can be secured to and/or released from the device housing by means of a rotational movement. The cover assembly and the device housing form an annular ring seal which is coaxial with the rotational movement and which is formed by an elastic sealing body having a circular sealing lip and a correspondingly circular shoulder seat on which the sealing lip is pressed due to the atmospheric differential pressure. Other aspects are disclosed and claimed.

20 Claims, 2 Drawing Sheets

(58) Field of Classification Search
USPC .............................. 356/335–343, 244, 247
See application file for complete search history.

WATER ANALYSIS DEVICE

The present application is a National Phase Entry of PCT International Application No. PCT/EP2017/071568, which was filed on Aug. 28, 2017, and which claims priority to Application No. 20 2016 105 143.6 in Germany on Sep. 15, 2016, the contents of which are hereby incorporated by reference.

FIELD OF THE INVENTION

The invention relates to an optical water analysis device with a light source and a light detector for the measurement of an optical parameter of a water sample in a transparent test cuvette. The invention relates in particular to a process turbidity measurement device.

BACKGROUND INFORMATION

A water analysis device of this kind is known from WO 2016/079259 A1. The water analysis device has a cuvette chamber in which a test cuvette is arranged. The water analysis device further has a ventilation circuit for the ventilation of the cuvette chamber, whereby the formation of condensate, in particular on the test cuvette, is avoided. The ventilation circuit has a ventilation pump downstream from the cuvette chamber. The cuvette chamber has an air inlet downstream from the ventilation pump. A device housing is provided which forms the cuvette chamber, and a cap arrangement is provided which closes and protects the cuvette chamber against atmospheric fluids. The fluid-tight sealing of the cap arrangement against the device housing is important in order for no air or dust that comes along with air and no humidity to penetrate the cuvette chamber or the interior of the device, because this causes severe disturbances to the scattering measurement. The cap arrangement must be easy to open so that simple access to the cuvette chamber and the test cuvette is possible.

The task of the invention is to create a water analysis device with a cap arrangement that offers a reliable sealing and an easy operability.

SUMMARY OF THE INVENTION

This task is inventively solved with a water analysis device having the features of claim 1.

The device housing forms and defines the cuvette chamber, among others, in which the test cuvette is arranged during the measurement procedure. The cap arrangement and the device housing have a screw-like mechanism, such that the cap arrangement can be closed and opened by a simple turning motion or, if applicable, locked to and unlocked from the device housing. The turning motion can be a screw motion, but it can also be a purely circular turning motion, in essence. In any case, a fixing or locking of the cap arrangement to the device housing is produced by the closing turning motion. A turning motion can be performed simply by a user, and relatively high turning forces can be applied by the user for the closing motion and opening motion. In this manner, a tool-free closing and opening of the cap arrangement on the device housing can be realized, in particular. A simple handling is hereby ensured, in particular in the case of maintenance work.

DETAILED DESCRIPTION

Figure 1:
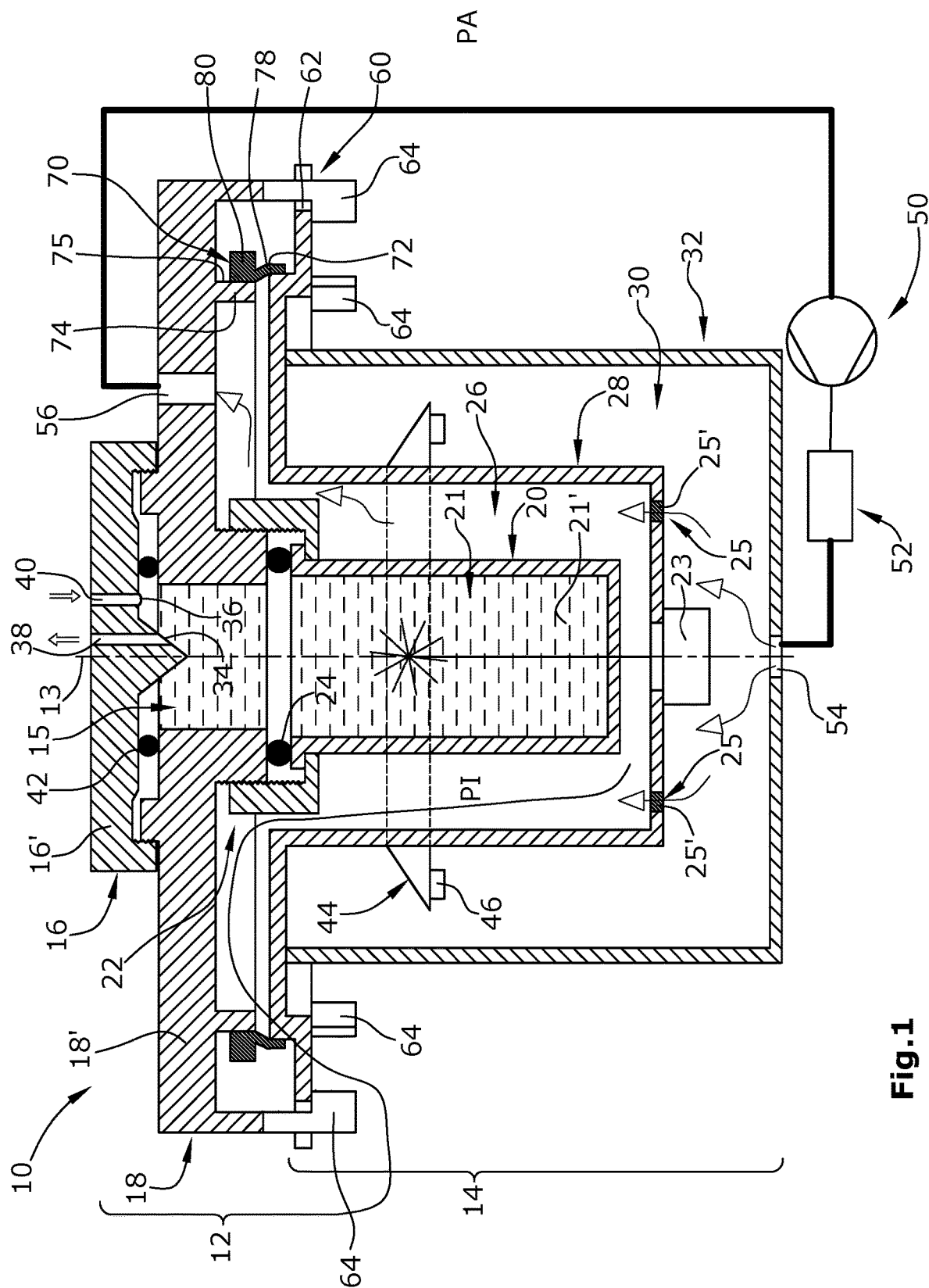
FIG. 1 illustrates 1 a longitudinal section of a schematically shown water analysis device with a ventilation circuit in a device housing that is closed by a cap arrangement.

The device housing on the one hand and the cap arrangement on the other hand form and define together an annular seal that is coaxial to the turning motion and ensures a fluid-tight sealing of the device interior when the cap arrangement is closed and locked.

The annular seal is formed on the one hand by a flexible and elastic sealing body with a circular sealing lip and on the other hand by a corresponding circular shoulder seat. During operation of the ventilation pump, there is always a certain low pressure in the cuvette chamber compared to the external atmospheric pressure. The sealing lip is pressed onto the corresponding circular shoulder seat by the atmospheric pressure, which is at least 2 mbar above the cuvette chamber interior pressure during operation of the ventilation pump, whereby the sealing effect of the ring seal is produced, improved, and perfected. It can hereby be practically ruled out that atmospheric air will enter the ventilation circuit from the outside, and in this manner dust and/or humidity will be introduced into the ventilation circuit.

When the ventilation pump is turned off, however, atmospheric pressure forms in the cuvette chamber after a certain period of release, such that there is no longer a difference in pressure between the cuvette chamber and the surrounding atmosphere. The circular sealing lip then only lies loosely upon the circular shoulder seat, such that the cap arrangement can be easily opened by a corresponding opening turning motion. Because the cuvette chamber is directly fluidically connected to the surrounding atmosphere during the closing of the cap arrangement and the ventilation pump remains turned off during the closing procedure, during the closing motion of the cap arrangement the sealing lip lies only loosely upon the corresponding circular shoulder seat, such that the adhesion between the sealing lip and the shoulder seat that prevents the turning motion is also negligible during the closing motion and the circular closing motion is only negligibly impeded.

In this manner, a water analysis device is created with relatively simple means, whose cap arrangement closing the cuvette chamber can be opened and closed through a simply and relatively low-resistance turning motion when the ventilation pump is turned off.

In principle, the sealing body can be provided on the device housing, and the corresponding circular shoulder seat can be provided on the sealing body. However, the sealing body is preferably provided on the cap arrangement, and the circular shoulder seat is preferably provided on the device housing.

The locking mechanism is preferably embodied as a bayonet lock. A bayonet lock offers the possibility of performing the opening and closing procedure through a relatively small turning motion, for example less than 100°.

According to a preferred embodiment, the sealing body has a clamping ring that is radially stretched onto a cylindrical support surface. It is particularly preferred for the clamping ring to be stretched inwards onto a radially internal cylindrical support surface. In this manner, the application of the sealing body onto the cylindrical support surface on the body in question, that is to say on the cap arrangement or on the device housing, is relatively simple. In particular, the exchange of the sealing body is relatively simple and dependable in this manner.

The shoulder seat is preferably convex and rounded when viewed in cross-section. When viewed in cross-section, the shoulder seat is formed such that the sealing lip can lie extensively or fully on the shoulder seat and does not detach from the shoulder seat, even if the differential pressure is relatively low. In this manner, a high sealing effect and sealing quality are realized in the long term.

The cuvette chamber air inlet, through which the cuvette chamber is ventilated with dry air, preferably has a pneumatic throttling element. This means, in principle, all elements that have a certain throttling effect upon air flow and in this manner cause a pressure difference between the upstream side and the downstream side. A high pressure is hereby built up between the ventilation pump and the pneumatic throttling element and a low pressure is built up downstream from the pneumatic throttling element, such that there is always a low pressure in the cuvette chamber when the ventilation pump is in operation. The pneumatic throttling element can, for example, be a membrane that is breathable but prevents the leakage of water from the cuvette chamber.

The test cuvette is preferably fixed to the cap arrangement such that upon opening and removal of the cap arrangement from the device housing, the test cuvette is also removed from the cuvette chamber. In this manner, the test cuvette is easy to remove and clean. The test cuvette can be fixed to the cap arrangement in an easily detachable manner, such that the test cuvette can be easily removed from the cap arrangement and cleaned or exchanged. Further, in this manner, the cuvette chamber is also more accessible after the cap arrangement has been removed from the device housing.

According to a preferred embodiment, the water analysis device is a process turbidity measurement device. In turbidity measurement devices, the introduction of dust into the cuvette chamber must be prevented at all costs, because the optical useful signal of a turbidity measurement is very small and can already be strongly distorted by very little dust. In a process device for turbidity measurement, the water sample is continuously pumped through the test cuvette. When the water sample is colder than the air in the cuvette chamber, this leads to condensation of humidity of the air located in the cuvette chamber.

In the ventilation circuit, a humidity absorption device is preferably provided, through which humidity is constantly removed from the ventilation circuit air. Through a reliable sealing arrangement, new humidity from the surrounding atmosphere is prevented from being introduced into the ventilation circuit, such that the intervals between exhaustion of the absorption device can be very long.

Figure 2:
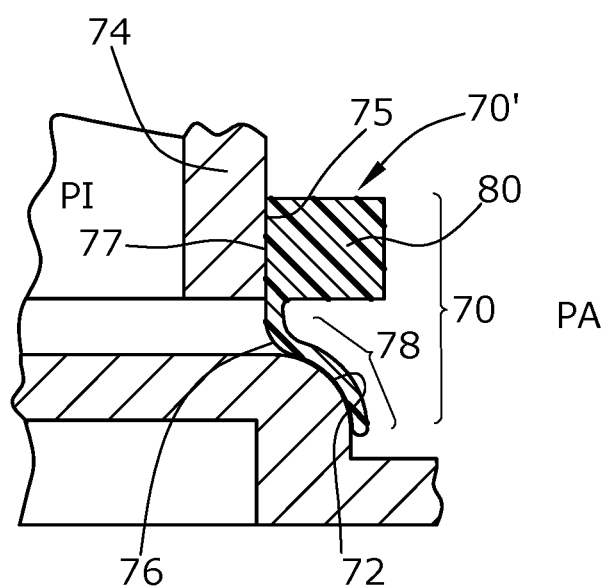
FIG. 2 illustrates an enlarged view of the ring seal between the cap arrangement and the device housing.

In the following, an exemplary embodiment of the invention is explained in further detail using the illustrations. The following are shown:

FIG. 1 a longitudinal section of a schematically shown water analysis device with a ventilation circuit in a device housing that is closed by a cap arrangement and FIG. 2 an enlarged view of the ring seal between the cap arrangement and the device housing.

FIG. 1 shows a schematic view of a water analysis device 10, which is embodied as a process turbidity measurement device in the present example and serves the measurement and determination of the turbidity of a water sample 21' in the cuvette interior 21 of a transparent and cylindrical test cuvette 20, which preferably consists of transparent, colorless glass. The water analysis device 10 is a process device in the present example, but it can also be embodied as a laboratory device, in principle. The water analysis device is particularly suited for use in an environment with a high relative or absolute humidity.

The water analysis device 10 is essentially structurally composed of a device housing 14, a fluid-tight cap arrangement 12 that closes the device housing 14, a ventilation pump 50, and a drying unit 52 downstream from the ventilation pump 50, which are arranged outside of the device housing 14.

In the interior of the housing, the water analysis device 10 has a cuvette chamber 26 defined by a cup-shaped cuvette chamber housing 28 in which the test cuvette 20 is arranged and has a test chamber 30 which surrounds the exterior of the cuvette chamber housing 28 and is, for its part, externally limited by a cup-shaped test chamber housing 32. The test chamber housing 32, the cuvette chamber housing 28, and the test cuvette 20 are all cup-shaped embodiments.

The water analysis device 10 has a ventilation circuit for the ventilation of the housing interior in order to prevent condensation of humidity in the test chamber 30 and in the cuvette chamber 26 on the surfaces therein.

The process water analysis device 10 is equipped with a sample inlet 40 and a sample outlet 38, through which the water sample flows continuously or non-continuously into the cuvette interior 21 of the test cuvette 20 and then flows out of it. The test cuvette 20 is arranged within the cuvette chamber 26, which is continuously ventilated with dry air by the ventilation circuit.

The cuvette chamber 26 is essentially formed by the cup-shaped transparent cuvette chamber housing 28 and closed by the cap arrangement 12. The test cuvette 20 hangs on the cap arrangement 12 and is detachably fixed via a flange nut 22. An annular sealing ring 24 is arranged between the opening collar of the test cuvette 20 and the annular flange on the main body 18 of the cap arrangement 12 and ensures a fluid-tight sealing in this area.

The turbidity of a liquid is a measurement for the concentration of solid particles in the water sample 21'. The turbidity is measured through the axial introduction of a light beam, which is emitted by a light source 23 axially along an optical longitudinal axis 13, into the test cuvette 20 and through the measurement of the light intensity of the light beam light scattered by the water sample 21' at an angle of 90° relative to the longitudinal axis 13, wherein the scattered light is collected by an annular optical element 44 and guided to an optical turbidity sensor 46. The annular optical element 44 and the turbidity sensor 46 are arranged in the test chamber 30.

The cap arrangement 12 essentially consists of an annular main cap 18 with a central opening 15 and a central cap 16 closing the central opening 15, which is screwed to the main cap 18.

The central cap 16 is formed by a cap body 16' made of opaque plastic and has the sample inlet 40 and sample outlet 38 on its exterior. The external sample inlet 40 leads to an internal sample inlet 36 through a conduit in the cap body 16, through which the water sample flows into the central opening 15 and into the cuvette interior 21. The external sample outlet 38 leads to an internal sample outlet 34 through a conduit in the cap body 16, through which the water sample flows out of the cuvette interior 21 through the central opening 15. An axial ring seal 42 is provided between the main cap 18 and the central cap 16 and ensures a fluid-tight sealing of the cuvette interior 21 against the external atmosphere.

The main cap 18 consists of a complex main cap body 18' made of opaque plastic and has, in particular, a locking mechanism 60 and a ring seal 70, both of which functionally interact with corresponding components on the device housing 14.

The locking mechanism 60 is embodied as a bayonet lock in the present example and has multiple axial bayonet teeth 64 on the cap side, each of which reaches behind a corresponding housing-side bayonet rib 62 in the locked closing position shown in FIG. 1. The locking mechanism 60 is embodied such that the opening and closing motion comprises an angle of only 15° to 30°, but particularly preferably 20°.

The ventilation circuit has the electric ventilation pump 50, the downstream passive drying unit 52 with molecular sieve, the pot-shaped test chamber 30, into which the air coming from the drying unit 52 flows through a device inlet opening 54 in the housing floor, the cuvette chamber 26, into which the air coming from the test chamber 30 flows through multiple air inlet openings 25 in the floor of the pot-shaped cuvette chamber housing 28, and a device air outlet 56, from which the drying air flows through a conduit to the ventilation pump 50.

In the air inlet openings 25 provided in the floor of the cuvette chamber housing 28, pneumatic throttling elements 25' are provided, which are formed by breathable membranes which are not, however, permeable to water molecules. The throttling elements 25' ensure a pressure drop in the one-digit to low three-digit millibar range when the ventilation pump 50 is running, such that there is a certain high pressure in the test chamber 30 compared to the atmospheric pressure PA and a certain low pressure in the cuvette chamber 26 compared to the atmosphere. In any case, when the ventilation pump 50 is running, the cuvette chamber pressure PI is lower than the atmospheric pressure PA outside of the water analysis device 10 by at least a few millibars.

The ring seal 70 is shown in detail in FIG. 2. It is essentially formed by a cap-side axial ring rib 74, a sealing body 70' fixed on the ring rib 74 with a circular sealing lip 78, and a housing-side circular and corresponding shoulder seat 72, upon which the flexible sealing lip 78 lies with its proximal lip surface 76. The shoulder seat 72 is convex and rounded when viewed in cross-section, as can be seen particularly well in FIG. 2. The radial size of the rounding is such that the full surface of the sealing lip 78 lies on the shoulder seat 72.

The elastic sealing body 70' essentially consists of a clamping ring 80, which is suspended and stretched with its proximal interior surface 77 onto a corresponding cylindrical distal support surface 75 of the ring rib 74, and the thin-lipped sealing lip 78. In the area of the ring seal 70, no grease of any kind is provided in order to improve the sealing effect, so the ring seal 70 is absolutely grease-free.

As long as the ventilation pump 50 is running, there is a low pressure in the cuvette chamber 26 compared to the atmospheric pressure PA, and there is a practically identical low pressure in the area of the circular shoulder seat 72 on the proximal lip surface 76 of the sealing lip 78. The full surface of the sealing lip 78 is hereby pressed onto the shoulder seat 72, whereby a very good fluid sealing is produced.

When the ventilation pump 50 is no longer running, more or less atmospheric pressure arises in the cuvette chamber 26 after a certain period of time, such that the sealing lip 78 only lies loosely on the shoulder seat 72. As a result, there is also no more static friction between the sealing lip 78 and the shoulder seat 72, such that the cap arrangement 12 can be held, turned in the direction of opening, and ultimately removed from the device housing 14 without any problems.

During the closing procedure, that is to say when the cap arrangement 12 is placed upon the device housing 14 and turned in the direction of closing, the ventilation pump 50 is turned off, such that it is also ensured during the closing procedure that the sealing lip 78 lies only loosely on the circular shoulder seat 72 and only negligible friction forces appear. As soon as the closing procedure is completed, the ventilation pump 50 can be turned on, such that a low pressure is generated in the cuvette chamber 26, whereupon the sealing lip 78 suctions itself to the shoulder seat 72.

If, during the measurement operation, there is a leak in the area of the ring seal 24 or the test cuvette 20 leaks, the liquid flowing into the cuvette chamber 26 with the high pressure can flow through the ring seal 70 without any problems, because here, the test chamber interior pressure PI is greater than the atmospheric pressure PA.

In this manner, the test sample liquids are prevented from flowing into other parts of the water analysis device 10 and triggering damage and disruption there.

The invention claimed is:

1. A water analysis device having a light source and a light detector which measures an optical parameter of a water sample in a transparent test cuvette, comprising:
 a cuvette chamber in which a test cuvette is arranged,
 a ventilation circuit which ventilates the cuvette chamber, wherein the ventilation circuit comprises the cuvette chamber, a ventilation pump downstream from the cuvette chamber, and a cuvette chamber air inlet downstream from the ventilation pump, wherein there is a differential pressure of at least 2.0 mbar in the cuvette chamber compared to the atmosphere when a ventilation pump is operated, and a cap arrangement and a device housing, wherein the device housing forms the cuvette chamber, which is fluidically closed by the cap arrangement, wherein
 the cap arrangement and the device housing have a screwlike mechanism, such that the cap arrangement can be locked and unlocked on the device housing by a turning motion, and
 the cap arrangement and the device housing form an annular ring seal that is coaxial to the turning motion, which is formed by an elastic sealing body with a circular sealing lip and a corresponding circular shoulder seat, upon which the sealing lip is pressed by the atmospheric differential pressure.

2. A water analysis device according to claim 1, wherein the locking mechanism is embodied as a bayonet lock.

3. A water analysis device according to claim 1, wherein the sealing body has a clamping ring, which is radially stretched onto a cylindrical support surface.

4. A water analysis device according to claim 2, wherein the sealing body has a clamping ring, which is radially stretched onto a cylindrical support surface.

5. A water analysis device according to claim 1, wherein the shoulder seat is convex and rounded when viewed in cross-section.

6. A water analysis device according to claim 2, wherein the shoulder seat is convex and rounded when viewed in cross-section.

7. A water analysis device according to claim 3, wherein the shoulder seat is convex and rounded when viewed in cross-section.

8. A water analysis device according to claim 4, wherein the shoulder seat is convex and rounded when viewed in cross-section.

9. A water analysis device according to claim 1, wherein the cuvette chamber air inlet has a pneumatic throttling element.

10. A water analysis device according to claim 2, wherein the cuvette chamber air inlet has a pneumatic throttling element.

11. A water analysis device according to claim 3, wherein the cuvette chamber air inlet has a pneumatic throttling element.

12. A water analysis device according to claim 4, wherein the cuvette chamber air inlet has a pneumatic throttling element.

13. A water analysis device according to claim 1, wherein the test cuvette is fixed to the cap arrangement.

14. A water analysis device according to claim 2, wherein the test cuvette is fixed to the cap arrangement.

15. A water analysis device according to claim 3, wherein the test cuvette is fixed to the cap arrangement.

16. A water analysis device according to claim 4, wherein the test cuvette is fixed to the cap arrangement.

17. A water analysis device according to claim 1, wherein the water analysis device is a process turbidity measurement device.

18. A water analysis device according to claim 2, wherein the water analysis device is a process turbidity measurement device.

19. A water analysis device according to claim 3, wherein the water analysis device is a process turbidity measurement device.

20. A water analysis device according to claim 1, wherein the water analysis device is a process turbidity measurement device.

\* \* \* \* \*